United States Patent [19]

Suen

[11] Patent Number: 5,017,699

[45] Date of Patent: May 21, 1991

[54] PROCESS FOR PREPARING POLYALKOXYMETHYLMELAMINES

[76] Inventor: Tzeng J. Suen, 349 Mariomi Rd., New Canaan, Conn. 06840

[21] Appl. No.: 554,681

[22] Filed: Jul. 19, 1990

[51] Int. Cl.$^5$ ............................................. C07D 251/64
[52] U.S. Cl. .................................................... 544/196
[58] Field of Search ........................................ 544/196

[56] References Cited

U.S. PATENT DOCUMENTS 3,824,232  7/1974  Pusch et al. ......................... 544/196
4,223,141  9/1980  Honel et al. ......................... 544/196

Primary Examiner—John M. Ford

[57] ABSTRACT

Polyalkoxymethylmelamines are prepared by reacting melamine with formaldehyde and then alkylating the resultant polymethylolmelamine with a lower monohydric alcohol, having 1 to 4 carbon atoms, especially methanol, in the presence of a solid "superacid" catalyst.

11 Claims, No Drawings

PROCESS FOR PREPARING POLYALKOXYMETHYLMELAMINES

BACKGROUND OF THE INVENTION

Polyalkoxymethylmelamines, especially polymethoxymethylmelamines, have been well known for their usefulness in serving as cross-linking agents in surface coatings and for treating paper and textile materials. See, for example, U.S. Pat. Nos. 2,715,619, 4,101,520; Canadian Pat. No. 773,170. Alkylation, especially methylation, of polymethylolmelamines improves the melamine-formaldehyde condensation products in their solobility characteristics, stability before application or curing, and efficiency in reacting with compounds containing active H atoms.

The alkylated polymethylolmelamines may be represented by the general formula $$MF_mR_n$$

where
- M = melamine
- F = combined formaldehyde, —CH$_2$O—
- R = alkyl group with 1 to 4 C atoms, CH$_3$ being the most important When M is lower than 4 and n/m ratio is lower than  or 0.67, their preparation is relatively easy. For most of the applications for which they are used, however, the degree of polymerization of the melamine-formaldehyde condensates should be kept low, preferably monomeric. For this reason, the reaction conditions for their preparation must be so chosen as not to promote undue polymerization. For condensates with m higher than 4 and n/m ratio higher than ⅔, methylation becomes laborious. Since the alkylation or ether formation reaction is reversible, the water formed during alkylation tends to drive the reaction backward and reach an equilibrium. In order to obtain fully-methylated products, water must be substantially removed from the reaction mass. As a rule, a second methylation step is carried out to complete the reaction and obtain the desired product. Strongly acidic conditions are required to effect the alkylation; but to remove the water by distillation, the pH should be above neutral in order to prevent polymerization. Repeated acidification and neutralization, with the accompanying salt formation, render the operation inconvenient.

Usually, nitric acid or hydrochloric acid is used as the catalyst for alkylation. (See, e.g., British Plastics, Feb. 1943, p. 518; U.S. Pat. No. 3,322,762, 4,101,520, 4,293,692; Canadian Pat. No. 773,170.) These acids require very careful handling. Hydrochloric acid is very corrosive to the reaction vessels. Nitric acid, being oxidizing, is dangerous to use with the oxidizable compounds formaldehyde and methanol. Furthermore, these acids are not anhydrous. The water introduced with the acid is unfavorable to the alkylation reaction equilibrium.

A process for preparing methylated polymethylol melamines using an organic acid cation exchange resin as the catalyst has been disclosed (U.S. Pat. No. 3,488,350) without the usual acidification. It is, however, not very efficient. A large amount of the catalyst, more than 10% by weight of the total reactions mass, is required.

SUMMARY OF THE INVENTION

It has now been found that by using a new class of solid "superacid" catalysts, alkylation of polymethylolmelamines can be efficiently and conveniently carried out without the need for neutralizing all the acid present in the reaction mass.

The superacid catalysts have been discovered in recent years (see G.A. Olah, et al., Science, 206, 1979, pp. 13-20). Their acidity has been estimated to be orders of magnitude higher than the mineral acids. Some of them are solids, such as perfluorinated resin sulfonic acid (e.g., Du Pont's Nafion-H), SbF$_5$-TiO$_2$-SiO$_2$, SbF$_5$-SiO$_2$-Al$_2$O$_3$ (see M. Hino and K. Arata, Chem. Soc. Japan Chem. Letters, 1979, pp. 1259-60). More recently developed solid superacid catalysts can be prepared more conveniently and more economically, notably "sulfate-treated" inorganic oxides, such as zirconia, titania, and iron oxide (see R.A.Rajadhyaksha et al., Ind. Eng. Chem. Res, 26 (9) 1987, pp. 1743-6; J. Am. Oil Chem. Soc., 65 (5) 1988, pp. 793-7; M. Hino and K. Arata, Chem. Soc. Japan. Chem. Letters, 1979, pp. 477-80; 1981, pp. 1671-2; J. Chem. Soc. Comm., 1979, pp. 1148-9; 1980, pp. 851-2). As catalysts for the preparation of the alkylated melamine-formaldehyde condensates, they are far superior to the mineral acids. They are stronger in acidity, they are not corrosive to the equipment. They are easily removable from the reaction mass, and they can be recycled.

The catalyst loading can be varied between 2% to 20%, preferably between 5 to 15%, based on the total weight of the reaction mass. The reaction temperature can be varied between 20°-60° C. Higher temperatures increase the rate of alkylation, but also tend to promote the formation of melamine resin polymers, while lower temperatures unduly extend the necessary reaction time.

The used catalyst can be regenerated, after filtration from the reaction mixture, by washing with methanol and preferably recalcining as is known in the art.

DESCRIPTION OF THE INVENTION INCLUDING PREFERRED EMBODIMENTS

In preparing the alkylated melamine-formaldehyde condensates in general, and methylated melamine-formaldehyde condensates in particular, the polymethylolmelamines may be prepared as usual, by reacting melamine with formaldehyde under neutral or slightly alkaline conditions. However, in the present invention, it has been found to be more convenient to carry out the methylolation reaction in the presence of the alkylating alcohol, with a small amount of water (5 to 20% by weight of the total reaction mixture) in the reaction mixture. It is followed by alkylation with an excess of alcohol in the presence of the superacid catalyst. Excess of alcohol is required to drive the reaction forward according to the mass action law. The higher the alcohol/formaldehyde ratio or alcohol/melamine ratio, the higher will be the n/m ratio in the finished product MFmRn. For products with m>4 and n/m>⅔, two-stage alkylation proves to be more economical than one-stage reaction with ultra high alcohol/melamine ratios.

The following examples are set forth for the purpose of illustration only and are not to be construed as limitations on the present invention except as set forth in the appended claims. All parts and percentages are by weight.

EXAMPLE A

Zr(OH)$_4$ is prepared by hydrolyzing ZrOCl$_2$.8H$_2$O with aqueous ammonia, followed by washing it free of alkali and drying at 100° C., and powdering the precipitate to below 100 mesh grains. The zirconium hydroxide is treated with 1-N sulfuric acid, followed by drying and calcination at 575° C. –650° C. in a Pyrex tube in air for 3 hours, and finally sealing until use.

EXAMPLE B

H$_4$TiO$_4$ is prepared by hydrolyzing TiCl$_4$ with aqueous ammonia followed by washing and drying. The precipitate is treated with sulfate ion by pouring 1-N H$_2$SO$_4$ (30 ml) on to the dried titanium hydroxide (2 g) on a filter paper. The material is dried and powdered below 100 mesh, calcined in a Pyrex tube in air at 600°–650° C. for 3 hours, and finally sealed in a glass tube until use.

EXAMPLE C

Fe(OH)$_3$ is precipitated by hydrolyzing ferric nitrate or chloride with aqueous ammonium hydroxide. It is washed and dired at 100° C. for 24 hours. The treatment of catalyst with sulfate ion is performed by pouring 30 ml of 0.5-N H$_2$SO$_4$ to 2 g of the dried Fe$_2$O$_3$ on a filter paper. After drying (without washing the treated material with water) the material is powdered below 100 mesh, calcined in air at 500° C. for 3 hours, and finally sealed until use.

EXAMPLE 1

Into a suitable reaction vessel equipped with thermometer, stirrer, and reflux condenser, methanol (320 parts, 10 moles) is introduced. The pH of the liquid is adjusted to 10.5–11.5 with a 50% NaOH solution. A charge of 330 parts of paraformaldehyde (91% CH$_2$O, 10 moles) is then added, and the mixture is heated to 45°–50° C. to effect complete solution. Melamine (126 parts, 1 mole) is introduced and the reaction mass is heated to 57° C. It exotherms to about 80° C. The reaction mixture is held at this temperature for about 15 minutes. A second portion of methanol (198 parts) is added, and the reaction mass is then cooled to about 35° C. A charge of 50 parts of sulfated zirconia superacid catalyst (as described in Example A) is introduced. The reaction mass is held at 35°–40° C. with stirring for 2 hours, and filtered to separate out the solid catalyst. The pH of the liquid is adjusted to 9–10 with 50% NaOH, concentrated under vacuum (30mm Hg pressure or lower) to a terminal temperature of 77° C. It is cooled to 35° C. and subjected to a second methylation step with 118 parts of methanol and 5 parts of fresh sulfated zirconia catalyst. The batch is held at 35°–40° C. with stirring for 1 hour. It is again filtered and the liquid adjusted to a pH of 9.5–10 and concentrated to a terminal temperature of about 100° C. under reduced pressure (30 mm Hg). The liquid product is centrifuged to remove any solid materials present. Its molar composition of melamine : formaldehyde : methanol is found to be 1 : 6.1 : 5.0.

EXAMPLE 2

Example 1 is repeated in substantially every essential detail except that sulfated TiO$_2$ catalyst (Example B) is used in place of sulfated ZrO$_2$. Similar results are obtained.

EXAMPLE 3

Example 1 is again repeated except that sulfated Fe$_2$O$_3$ is used as the methylation catalyst. Similar results are obtained.

EXAMPLE 4

The procedure of Example 1 is again followed except that the methanol is replaced by n-butanol. Butylated polymethylol melamine is recovered.

EXAMPLE 5

Example 1 is repeated except that in the second methylation step 315 parts of methenol and 7 parts of sulfated zirconia catalyst are used. The product has a molar composition of MF$_{6.0}$Me$_{5.6}$.

EXAMPLE 6

Example 1is repeated except that in the second methylation step 79 parts of methanol and 4 parts of sulfated zirconia catalyst are used. The product has a molar composition of MF$_{6.0}$Me4.6.

I claim:

1. A process for preparing polyalkyl ethers of polymethylol melamine compounds, comprising reacting a polymethylol melamine with a quantity of a monohydric alcohol having 1 to 4 carbon atoms in the presence of a solid superacid catalyst.
2. The process according to claim 1 wherein the catalyst is an inorganic solid superacid material.
3. The process according to claim 1 wherein the catalyst is sulfated Zr0$_2$, sulfated Ti0$_2$ or sulfated Fe2O3.
4. The process according to claim 1 wherein the polymethylol melamine is hexamethylol melamine.
5. The process according to claim 1 wherein the alcohol is methanol.
6. The process according to claim 1 wherein the alcohol is n-butanol.
7. The process according to claim 1 wherein the alcohol is a mixture of alcohols having 1 to 4 carbon atoms.
8. The process according to claim 1 wherein the polymethylol melamine is prepared in the substantial absence of water.
9. The process according to claim 1 wherein the catalyst is sulfated ZrO$_2$.
10. The process according to claim 1 wherein the catalyst is sulfated TiO$_2$.
11. The process according to claim 1 wherein the catalyst is sulfated Fe$_2$O$_3$.

* * * * *